US012397173B2

(12) United States Patent
Gahl et al.

(10) Patent No.: US 12,397,173 B2
(45) Date of Patent: Aug. 26, 2025

(54) NEUTRON CAPTURE THERAPY FOR INFECTION CONTROL OF SURGICAL IMPLANTS

(71) Applicant: The Curators of the University of Missouri, Columbia, MO (US)

(72) Inventors: John Gahl, Columbia, MO (US); John Brockman, Columbia, MO (US); Michael Flagg, Columbia, MO (US); David A. Volgas, Columbia, MO (US); James Stannard, Columbia, MO (US); Charles Maitz, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 1228 days.

(21) Appl. No.: 16/349,445

(22) PCT Filed: Nov. 14, 2017

(86) PCT No.: PCT/US2017/061454
§ 371 (c)(1),
(2) Date: May 13, 2019

(87) PCT Pub. No.: WO2018/089972
PCT Pub. Date: May 17, 2018

(65) Prior Publication Data
US 2019/0269938 A1 Sep. 5, 2019

Related U.S. Application Data

(60) Provisional application No. 62/421,620, filed on Nov. 14, 2016, provisional application No. 62/574,176, filed on Oct. 18, 2017.

(51) Int. Cl.
| | | |
|---|---|---|
| *A61N 5/10* | (2006.01) | |
| *A61K 41/00* | (2020.01) | |
| *A61K 47/69* | (2017.01) | |
| *A61L 27/50* | (2006.01) | |
| *A61L 27/54* | (2006.01) | |
| *A61L 31/16* | (2006.01) | |
| *A61L 31/14* | (2006.01) | |
| *G21G 4/08* | (2006.01) | |

(52) U.S. Cl.
CPC .............. *A61N 5/10* (2013.01); *A61K 41/009* (2013.01); *A61K 41/0095* (2013.01); *A61K 47/6957* (2017.08); *A61L 27/50* (2013.01); *A61L 27/54* (2013.01); *A61L 31/16* (2013.01); *A61L 31/14* (2013.01); *A61L 2300/44* (2013.01); *A61N 2005/109* (2013.01); *G21G 4/08* (2013.01)

(58) Field of Classification Search
CPC .......... A61N 5/10; A61K 47/69; A61K 41/00; A61L 27/54
See application file for complete search history.

(56) References Cited

U.S. PATENT DOCUMENTS

| | | | |
|---|---|---|---|
| 5,217,493 A * | 6/1993 | Raad | A61K 31/70 623/11.11 |
| 6,183,409 B1 | 2/2001 | Armini | |
| 6,187,037 B1 | 2/2001 | Satz | |
| 6,997,861 B2 | 2/2006 | Halpern et al. | |
| 7,022,136 B2 * | 4/2006 | Lundqvist | G21G 4/08 623/1.42 |
| 7,530,940 B2 | 5/2009 | Hainfeld et al. | |
| 7,776,310 B2 * | 8/2010 | Kaplan | A61L 31/10 600/7 |
| 8,445,008 B2 * | 5/2013 | Ferris | A61L 29/14 424/422 |
| 8,512,294 B2 | 8/2013 | Ou-Yang | |
| 8,668,935 B2 | 3/2014 | Peyman | |
| 2002/0103410 A1 * | 8/2002 | Munro, III | A61N 5/1015 600/3 |
| 2003/0012325 A1 | 1/2003 | Kernert et al. | |
| 2003/0088145 A1 * | 5/2003 | Scott | A61N 1/406 600/8 |
| 2006/0127307 A1 * | 6/2006 | Canham | A61K 31/695 424/1.49 |
| 2013/0102829 A1 | 4/2013 | Chou et al. | |
| 2015/0314047 A1 | 11/2015 | Lin et al. | |
| 2016/0051384 A1 * | 2/2016 | Patel | C22C 27/00 148/668 |

FOREIGN PATENT DOCUMENTS

| | | |
|---|---|---|
| WO | WO 2001070336 A1 | 9/2001 |
| WO | WO 2002042318 A2 | 5/2002 |

OTHER PUBLICATIONS

Jeffrey A. Coderre et al. Boron Neutron Capture Therapy: Cellular Targeting of High Linear Energy Transfer Radiation, Technology in Cancer Research and Treatment, vol. 2(5) 355-375. (Year: 2003).*
S. Halfon et al. High power accelerator-based boron neutron capture with a liquid lithium target and new applications to treatment of infectious diseases, Applied Radiation and Isotopes, 67, S278-S281. (Year: 2009).*
Gonsalves, et al., "Synthesis of Titanium and Boron Containing Polymers: Potential Precursors for Advanced Ceramics", Mat. Res. Soc. Symp. Proc. vol. 120, 1988 Materials Research Society (5 pgs).

(Continued)

*Primary Examiner* — Michael G. Hartley
*Assistant Examiner* — Jagadishwar R Samala
(74) *Attorney, Agent, or Firm* — Sandberg Phoenix & von Gontard, PC; Steven T. Kamierski

(57) ABSTRACT

The present invention provides an implant comprising an isotope capable of producing a dose of ionizing radiation upon exposure to a flux of low energy neutrons, and a method in which, after implantation, the implant is exposed to a flux of low energy neutrons to control or treat infections.

18 Claims, 6 Drawing Sheets

(56) References Cited

OTHER PUBLICATIONS

International Search Report and Written Opinion issued for corresponding PCT/US17/61454 dated Jan. 25, 2018 (16 pgs).

Halfon, S., et al., "High power accelerator-based boron neutron capture with a liquid lithium target and new applications to treatment of infectious diseases". Applied Radiation and Isotopes. Jul. 2009, vol. 67 (7-8 Suppl), pp. S278-S271, DOI: 10.1016/j.apradiso.2009.03.075.

Hawthorne, M.F., et al., "A critical assessment of boron target compounds for boron neutron capture therapy", Journal of Neuro-Oncology 62: 33-45, 2003.

Shirwaiker, R., et al., "Nanomaterials and synergistic low intensity direct current (LIDC) stimulation technology for orthopaedic implantable medical devices", Wiley Interdiscip Rev Nanomed Nanobiotechnol. Author manuscript; available in PMC, May 1, 2014.

Halfon, S., et al., "High power accelerator-based boron neutron capture with a liquid lithium target and new applications to treatment of infectious diseases", Applied Radiation and Isotopes 67 (2009) S278-SS281.

Publication entitled "Current status of neutron capture therapy", IAEA-TECDOC-1223, International Atomic Energy Agency, May 2001.

Chan, K., "Polypropylene Biocomposites with Boron Nitride and Nanohydroxyapatite Reinforcements", Materials 2015, 8, 992-1008; doi:10.3390/ma8030992.

Angrisani, N., et al., "Rare Earth Metals as Alloying Components in Magnesium Implants for Orthopaedic Applications", http://dx.doi.org/10.5772/48335.

* cited by examiner

NEUTRON CAPTURE THERAPY FOR INFECTION CONTROL OF SURGICAL IMPLANTS

CROSS-REFERENCE TO RELATED APPLICATIONS

This application is based on and claims priority to U.S. Provisional Application Ser. No. 62/421,620 filed on Nov. 14, 2016 and 62/574,176 filed on Oct. 18, 2017, which are hereby incorporated herein by reference.

BACKGROUND OF THE INVENTION

1. Field of the Invention

The present invention relates to a device and method for infection control of surgical implants.

2. Description of Related Art

The statements in this section merely provide background information related to the present disclosure and may not constitute prior art.

Biological implants can serve as a nidus for infection. Direct inoculation can occur during the medical procedure or by hematogenous inoculation from various infections elsewhere in the body, even years after the implantation. Infections at the implant site, especially at the implant surface, can result in formation of a biofilm, a highly hydrated extracellular structure affixed to the surface of the implant. Infections that have formed a biofilm are difficult to treat with antibiotics. Accumulation of waste products and other substances in this structure cause microbes to either stop growing or force them into a low-growth mode, resulting in a microorganism that is up to 1,000 times more resistant to growth-dependent antimicrobial agents than non-biofilm organisms. In many cases, treating such an infection requires costly remediation (such as additional surgery, removal of implants, and hospitalization). In 2013 it was estimated that $9.8B was spent treating hospital acquired infections, with surgical site infections being the leading cause.

Boron neutron capture therapy (BNCT) has been studied previously, mostly for cancer therapy, with limited practical success. BNCT is a binary therapy that requires placement of $^{10}$B in or near the tumor cell and a source of thermal neutrons at the treatment area. BNCT uses $^{10}$B, a stable (non-radioactive) isotope of boron which has a 3837 b cross-section for capturing thermal neutrons. Since BNCT is a binary therapy, the deliverable dose to the target volume is dependent on the $^{10}$B atom density and the thermal neutron flux in the tumor volume. The neutrons primarily interact with $^{10}$B resulting in high LET radiation dose at the location of the boron atom, having minimal effect elsewhere. Thermal neutrons absorbed by $^{10}$B produce $^7$Li (1.02 MeV)+$^4$He (1.78 MeV) with a branching ratio of 94% and $^7$Li (0.84 MeV)+$^4$He (1.47 MeV)+0.48 MeV gamma ray with a branching ratio of 6%. The Li and He ions deposit kinetic energy within 5 μm and 10 μm of tissue, respectively. While this distance corresponds to approximately five cell diameters of *S. aureus*, the dose rate decreases dramatically beyond 3 μm, imparting specificity to treatment of cells containing or directly in contact with $^{10}$B.

In BNCT, targeted dose delivery relies on the delivery of $^{10}$B specifically to the target tissues, and non-specific dose unrelated to boron content will, ideally, only slightly affect the delivered radiation dose. Previous studies have demonstrated that BNCT can be administered safely. However, injection of a drug containing $^{10}$B is expected to localize at the tumor site a concentration of 0.001 wt %. In addition, because the approved boron compounds have limited selectivity for the tumor target and limited mobility across the blood brain barrier, BNCT has not been shown to be more effective than conventional radiotherapies.

BRIEF SUMMARY OF THE INVENTION

The present invention provides a device and method to treat infection at implant sites. The inventive system comprises an implant comprising an isotope capable of producing a dose of ionizing radiation upon exposure to a flux of low energy neutrons. Preferably the implant comprises a material enriched in the isotope. The implant may be exposed to a flux of low energy neutrons when an infection occurs after implantation. The implant may comprise a surface layer doped with the isotope. Suitable isotopes include boron-10 (B-10), lithium-6 (Li-6), gandolinium-157 (Gd-157) and dysprosium-164 (Dy-164).

The invention further provides a method for infection control and/or treatment of an implant site. The inventive method for control and/or treatment of an implant site comprises the steps of i) implanting an implant comprising an isotope capable of producing a dose of ionizing radiation upon exposure to a flux of low energy neutrons, including implants of the present invention, and ii) exposing the implant site to a flux of low energy neutrons after implantation, such as when an infection occurs after implantation.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
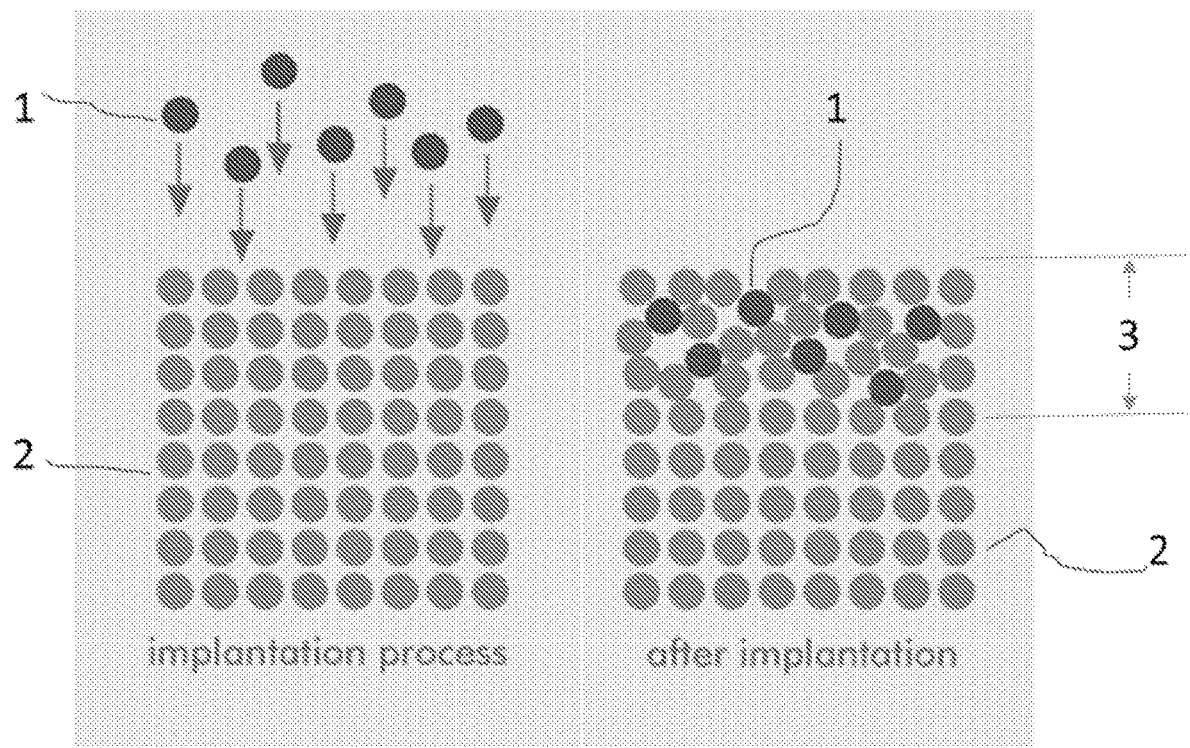
FIG. 1 is a schematic illustration of an exemplary B-integrated surface layer.

The following description is merely exemplary in nature and is in no way intended to limit the present teachings, application, or uses. Throughout this specification, like reference numerals will be used to refer to like elements.

The present disclosure provides a device and method employing NCT technology for infection control and/or treatment at implant sites. The inventive device integrates an isotope capable of producing a dose of ionizing radiation upon exposure to a flux of low energy neutrons into an implant suitable for implantation into a human or animal body. Suitable isotopes have high interactive probability (e.g. capture cross section) with neutrons, and upon neutron capture, undergo energetic decay. In certain embodiments the implant comprises a material enriched with isotope to thereby increase the concentration of isotope and the dosage emitted during any period of time. Suitable isotopes include B-10, Li-6, Gd-157 and Dy-164.

When infection occurs after implantation, the method of the present invention employs neutron capture therapy to expose the implantation site with flux of low energy neutrons to effectively sterilize the surface of the implant and rid of infection. The implant of the present invention is capable of producing a dose of ionizing radiation upon exposure to a flux of low energy neutrons, wherein the dose of ionizing radiation is suitable for treating bacterial infection at an implantation site after implantation. The isotope is only located at the implant, where the infection is, sparing healthy tissue from radiation dose. Incorporation of the isotope into the implant places large concentrations of the isotope precisely at the nidus of infection.

By concentrating the isotope near the surface of the implant, the implant and method of the present invention allow a large dosage of radiation during a short period of time, resulting in a lower background dose.

It was surprisingly found that use of the implant of the present invention in the method of the present invention resulted in bacterial survival data that did not match the expected bacterial survival curve. Although modeling data showed the high LET particles from the NCT capture reaction travel about 6 um into glycerin, actual experimental data showed the NCT method of the present invention unexpectedly resulted in cell death beyond 6 um, where bacteria do not directly interact with the high LET NCT products.

In certain embodiments discussed herein, the isotope is B-10. However, it should be understood that the following discussion is applicable to implants comprising other isotopes, including Li-6, Gd-157 and Dy-164.

The device of the present invention comprises an implant body, which may include all or any portion of the implant. Boron may be present throughout the implant body or only a portion of the implant near the surface of the implant. In certain embodiments, the inventive system comprises an implant with boron-integrated surface layer (which includes at least the surface and subsurface of the implant). The depth of the surface layer integrated with Boron ranges from 1 to 100 μm in thickness, or greater, varying based on the desired material characteristics of the implant material. For example, when Ti is used as the implant material, the thickness of the Boron integrated layer may be approximately less than 5 μm. The surface layer should be sufficiently thick to ensure boron remains at the surface after abrasion or wear during use or implantation. In certain embodiments, the surface layer is greater than 1 μm thick, 1 to 100 μm thick, 1 to 50 μm, 1 to 20 μm, 1 to 10 μm, or 3 to 7 μm thick, and any value or range therebetween.

Natural boron with approximately 20% B-10 isotope may be employed in the implant of the present invention. However, boron enriched with B-10 is preferred to increase the concentration of the B-10 isotope resulting in a higher dosage than natural boron. When used herein, term "enriched" means having a concentration of B-10 (or other isotope) in higher concentrations than found in the naturally occurring forms of the element. In certain embodiments, the boron comprises greater than 20% B-10, 30% or greater B-10, 50% or greater B-10, or 90% or greater B-10 or any range or value therebetween. In certain embodiments, highly enriched boron, for example with 95% enriched B-10, is used. Any material that contains B-10 can be used, including, titanium borides ($TiB_2$ or TiB), borided steel, other metal borides, borated polyethylene, boron polymers, and other polymers containing borate or boron nitride.

Various method or technology may be employed to incorporate boron into the implant. In certain embodiments, boron may be present throughout the implant or in a portion of the implant. In certain embodiments, the source of $^{10}B$ is a layer of boron containing ceramic material (for example, $TiB_2$) or boron containing alloy with a transition metal (for example Fe and boron containing steel) and other materials with high boron atom density. Other materials comprising boron may be used. In certain embodiments, the surface of the implant is modified to incorporate boron. Conventional methods, such as beam line ion implantation and plasma immersion ion implantation, may be employed, as well as thermal diffusion processes and various chemical processes. For example, an ion implantation or chemical diffusion process may be used to "harden" the surface of the implant, which may be particularly useful when using Li-6. The highest boron concentrations are likely to come from modifying, for example, the titanium metal surface from Ti metal to $TiB_2$ using a thermal diffusion process. Refer to FIG. 1, which illustrates an exemplary Boron ions implanting into a surface layer. As shown in FIG. 1, Boron ions, 1, are implanted into the surface layer, 3, of a device, 2.

The implant may be any conventional implant, or any device that functions as a structural implant in the body, such as an orthopedic implant, a stent, or catheter. However, in certain embodiments, the implant is not an orthopedic implant and/or is not a stent. Because the purpose of the invention is to prevent or treat infection at an implantation site, the implant is intended for, and has a structure designed for, a primary purpose apart from delivery of BNCT. The invention does not encompass an implant designed only to deliver BNCT without another purpose. The implant may be made out of a variety of materials, such as metals, ceramics, polymers, or a combination thereof.

As discussed above, other isotopes having high interactive probability (e.g. capture cross section) with neutrons, such as Li-6, Gd-157 and Dy-164, can be used in the embodiments discussed above with respect to B-10. For example, Gd-157 has a high neutron capture cross section of 254,000 barnes, which produces internal conversion and auger electrons with path lengths of approximately 1 cell diameter.

The inventive method will also be described with respect to an implant comprising B-10, but the discussion is applicable to implants comprising the other isotopes discussed herein. The inventive method for control and/or treatment of infection at an implant site comprises the steps of i) implanting an implant comprising boron-10 into an human or animal subject, and ii) exposing the implant site to a flux of low energy neutrons to produce a dose of high LET and ionizing radiation suitable for treating bacterial infection at the implantation site after implantation. The method of the present invention can utilize any of the devices described or contemplated above or in the Examples below, including implants comprising, Li-6, Gd-157 and Dy-164.

The exposing step may be conducted prophylactically immediately after implantation or at the first signs of infection after implantation without removal of the implant or reopening of the implantation site. The exposing step may be conducted repeatedly over many years. Furthermore, the Boron-containing implants may be irradiated by thermal neutron sources in hospital prior to implantation to sterilize surfaces before surgery (when the conventional autoclave process is not available).

The boron neutron capture therapy for infection control is a bimodal treatment modality that combines a $^{10}$B nuclei at the treatment site with thermal neutrons. As discussed above, the source of $^{10}$B may be a layer of boron containing ceramic material (for example, $TiB_2$) or boron containing alloy with a transition metal (for example Fe and boron containing steel) and other materials with high boron atom density. The source of neutrons could be a reactor or an accelerator. Suitable beams are known in the art, such as those described on pages 7 and 8 of *Current Status of Neutron Capture Therapy*, International Atomic Energy Agency, May, 2001, which is incorporated by reference for such disclosure.

The method of the present invention can deliver both shallow and deep neutron treatment to irradiate infection using differing energy levels. In certain embodiments used for shallow implants, the treatment relies on thermal neutrons (energy range 0.001 eV-0.5 eV) at the implant to initiate the nuclear reaction $^{10}$B(n,alpha)$^{7}$Li. Thermal neutrons have a range in tissue of 1 cm to 2 cm. For deeper implants are that are 1 cm, 2 cm, or more, away from the surface of the organism (depth from surface>1 cm, or >2 cm) the implant may be treated with higher energy (epithermal) neutrons. The epithermal neutrons penetrate tissue (in certain embodiments are expected to penetrate 7-8 cm) to treat deeper implants. Epithermal neutrons have an energy range from 0.5 eV up to 100 keV. Ranges of neutrons from 0.5 eV to 100 eV and from 100 eV up to 100 keV may be used.

The aforesaid low energy neutrons may be produced by any low energy neutron source, such as nuclear reactors, electron beam accelerator facilities, or ion beam accelerators. Appropriate design and modification of the conventional low energy neutron sources may be adopted for the therapy. In certain embodiments, the flux of low energy neutrons produced at the implantation site during the exposing step is $1\times10^8$ to $15\times10^8$ neutrons $cm^{-2}$ $s^{-1}$, $8.0\times10^8$ to $9.0\times10^8$ neutrons $cm^{-2}$ $s^{-1}$, or is $8.4\times10^8$ neutrons $cm^{-2}$ $s^{-1}$.

Figure 2:
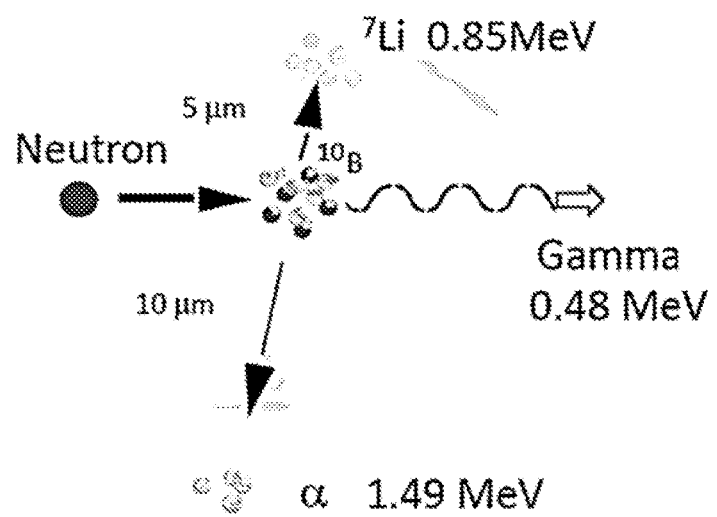
FIG. 2 is a schematic illustration of the basic mechanism of BNCT.

FIG. 2 illustrates the basic mechanism of the BNCT. As shown in FIG. 2, after neutron capture in B-10 with high probability of neutron capture, there is an immediate emission of alpha particles and recoiling Li-7 ions. These high energy ions result in the sterilization of the surface. The range of these ions in tissue is approximately or less than 10 microns, which is sufficient to eradicate the common bacteria, such as *Staphylococcus* with width and length roughly on the order of 1 micron.

In certain embodiments, the dose delivered in the exposing step within 6 μm of a surface of the implant is greater than 2 kGy, 2 to 60 kGy, 2 to 20 kGy, 5 to 15 kGy, or 10 to 15 kGy, or any range or value therebetween.

In certain embodiments, the thermal neutron fluence delivered in the exposing step is greater than $7.5\times10^{11}$ n/cm$^2$, greater than $1.5\times10^{12}$ n/cm$^2$, $2.6\times10^{12}$ n/cm$^2$ to $3.0\times10^{12}$ n/cm$^2$ or greater than $3.0\times10^{12}$ n/cm$^2$, or any range or value therebetween.

In certain embodiments, the implant is exposed to the flux of low energy neutrons for 1 minute to 120 minutes, for 1 minute to 60 minutes, for five minutes to 30 minutes or for 10 minutes to 15 minutes, or any range or value therebetween.

In certain embodiments, the dose within 6 μm of the surface of the device is greater than 2 kGy, 2 to 60 kGy, 2 to 20 kGy, 5 to 15 kGy, greater than 10 kGy, 10 to 60 kGy, 10 to 20 kGy, 10 to 15 kGy, or any range or value therebetween and the exposure is less than 30 minutes, less than 20 minutes, less than 15 minutes, less than 10 minutes or less than 5 minutes, or any value or range therebetween. In certain embodiments, the dose within 6 μm of the surface of the device is as described in the previous sentence, and a background dose delivered within 6 μm of the surface is less than 100 cGy, less than 75 cGy, less than 50 cGy or less than 25 cGy, or any value or range therebetween.

The Boron-containing implant and BNCT method of the present invention are effective in infection control/treatment of the implant site. As further described in the Examples, staph bacterium colonies on titanium diboride exposed to a thermal neutron flux showed a 3000 fold reduction compared to a control held outside of the neutron field. Staph colonies on pure titanium samples showed no difference between irradiated and non-irradiated samples. Most common bacteria grown on the surface of the implant may be treated using the inventive device and method. In certain embodiments, the survival fraction of bacteria at the implantation site after the exposing step is $0.62\times10^{-5}$ to $3.1\times10^{-5}$ compared to a non-irradiated control, less than 0.46 compared to a control, less than 0.21 compared to a control, less than 0.02 compared to a control, or less than $2.3\times10^3$ compared to a control, or any value or range therebetween. In certain embodiments, 0.3% or fewer of the bacterial at the implantation site survive the exposing step, 0.2% or fewer or 0.004% or fewer survive or any range or value therebetween.

The inventive system/method with Boron-modified implant and BNCT is safe for patients. First, the low energy neutrons, such as thermal or epi-thermal neutrons, exposed to the implant site have little biological effect in humans. Secondly, the radiation range/effect of the resulting emission (the alpha particles and recoiling Li-7 ions) is short, approximately 10 microns, and limited to the surface of implant, where the infection is, which reduces exposure to other areas of a patient's body. Furthermore, the treatment can be repeated multiple times after implantation, which dramatically reduces cost of dealing with infections.

EXAMPLES

Example 1. Dose Modeling and Microbiology Studies

Facilities. We used the thermal neutron beamline for neutron capture therapy cell and small-animal radiobiology studies at the University of Missouri Research Reactor (MURR) center. The irradiation position is described in detail elsewhere. The beamline features the use of single-crystal silicon and bismuth sections for neutron filtering and for reduction of incident gamma radiation. The measured thermal neutron fluxes produced at the irradiation location is $8.4\times10^8$ neutrons $cm^{-2}$ $s^{-1}$. The background gamma dose for the facility is 2.7 cGy/min and the background physical neutron dose is 2.5 cGy/min. The beamline has a well-thermalized neutron spectrum with sufficient thermal neutron flux for a variety of BNCT studies.

Dose Modeling Study. In silico dose modeling of the experiment was performed prior to in vitro studies. The physical radiation dose was calculated using the Monte Carlo N-Particle (MCNPX 2.7) radiation transport code. The MCNPX model used the unfolded neutron spectrum measured at the thermal neutron beam facility at the MURR center. The model geometry consisted of a 1 cm diameter $TiB_2$ disk positioned in the neutron beam. The $TiB_2$ target was covered with a 30 μm thick layer of glycerin that was sub-divided into 2 μm thicknesses, about the size of two *S. aureus* cells. The model was normalized using a constant derived from the measured neutron flux in the irradiation facility using a Cu/Au flux wire. The neutron flux in the MCNPX model was monitored above the $TiB_2$ material using an F4 tally. The calculated physical dose (Gy) from the $^7Li$ nuclei and the alpha particle produced from the $^{10}B$ neutron capture reaction in the glycerin layer above the $TiB_2$ surface was determined using the neutron capture ion algorithm (NCIA) option in MCNPX. The $7^{th}$ entry on the phys:n card was set to 5 to transport the alpha particles and $^7Li$ nuclei while preserving angular momentum. The physical radiation dose was calculated as the sum of the kinetic energy deposited by the α particle and the $^7Li$ ion in the glycerin volume above the $TiB_2$ surface.

neutron flux in these experiments was $8.4 \times 10^8$ n/cm²/s. The thermal neutron fluence in the 15 minute irradiation was $7.5 \times 10^{11}$ n/cm², in the 30 minute irradiation was $1.5 \times 10^{12}$ n/cm², in the 45 minute irradiation was $2.3 \times 10^{12}$ c/cm², and in the 60 minute irradiation was $3.0 \times 10^{12}$ n/cm². After irradiation, bacteria on each disk was collected by a sterile swab and suspended in 1 mL of physiological saline, tenfold serially diluted, and 10 μL of each dilution was plated on LB agar plates and cultured. The numbers of bacterial colonies were enumerated after 16 h of incubation at 37° C. The antimicrobial activity was expressed as surviving fraction using the following formula: (CFU on $TiB_2$ with irradiation)/(CFU on TiB2 without irradiation). No Institutional Review Board, Animal Care and Use Committee, or other ethics review board approval was required for these studies.

Dose Modeling Results. The calculated physical dose in the first 6 μm of glycerin extending from the $TiB_2$ surface is reported in Table 1 and FIG. 4. MCNPX was also used to calculate the physical dose in two additional theoretical scenarios; a 90% enriched $^{10}B$ containing $TiB_2$ target, and a Ti metal target with a 10 μm thick coating of 90% enriched $^{10}B$ containing $TiB_2$. The physical dose rates for these theoretical materials are also reported in Table 1.

TABLE 1

Physical dose calculated using MCNPX.

| Material | $^{10}B$ enrichment | Dose (Gy/min) 0-2 μm | Dose (Gy/min) 2-4 μm | Dose (Gy/min) 4-6 μm | Dose (Gy/min) Total |
|---|---|---|---|---|---|
| Bulk $TiB_2$ | Natural 20% $^{10}B$ | 164 | 34.1 | 3.6 | 201 |
| Bulk $TiB_2$ | 90% $^{10}B$ | 914 | 186 | 204 | 1120 |
| 10 μm $TiB_2$/Ti metal | 90% $^{10}B$ | 779 | 161 | 16.6 | 957 |

Microbiology Study. The *Staphylococcus aureus* (*S. aureus*, ATCC 29213) bacterial culture was maintained on Trypticase Soy Agar (TSA) with 5% Sheep Blood (Thermo Fisher Scientific) plates at 37° C. Microbiology studies involved 18 disks inoculated with *S. aureus* in a thin layer of glycerin. The glycerin maintained the viability of the bacteria by retaining moisture at the surface of the $TiB_2$ disk. The antimicrobial activity of $TiB_2$ with irradiation was determined by a colony-forming unit (CFU) counting assay. Prior to inoculating onto the $TiB_2$ disks, a 20 μL aliquot of $2 \times 10^6$ CFU/mL bacterial suspension in the minimal growth medium (100-fold diluted Mueller-Hinton broth) was mixed with 5 μL glycerol (final concentration=20%). The mixture was inoculated on the surface of the $TiB_2$ or Ti (control) disks. Each treatment or control group consisted of three disks mounted inside of a sterile petri dish using epoxy resin.

Figure 3:
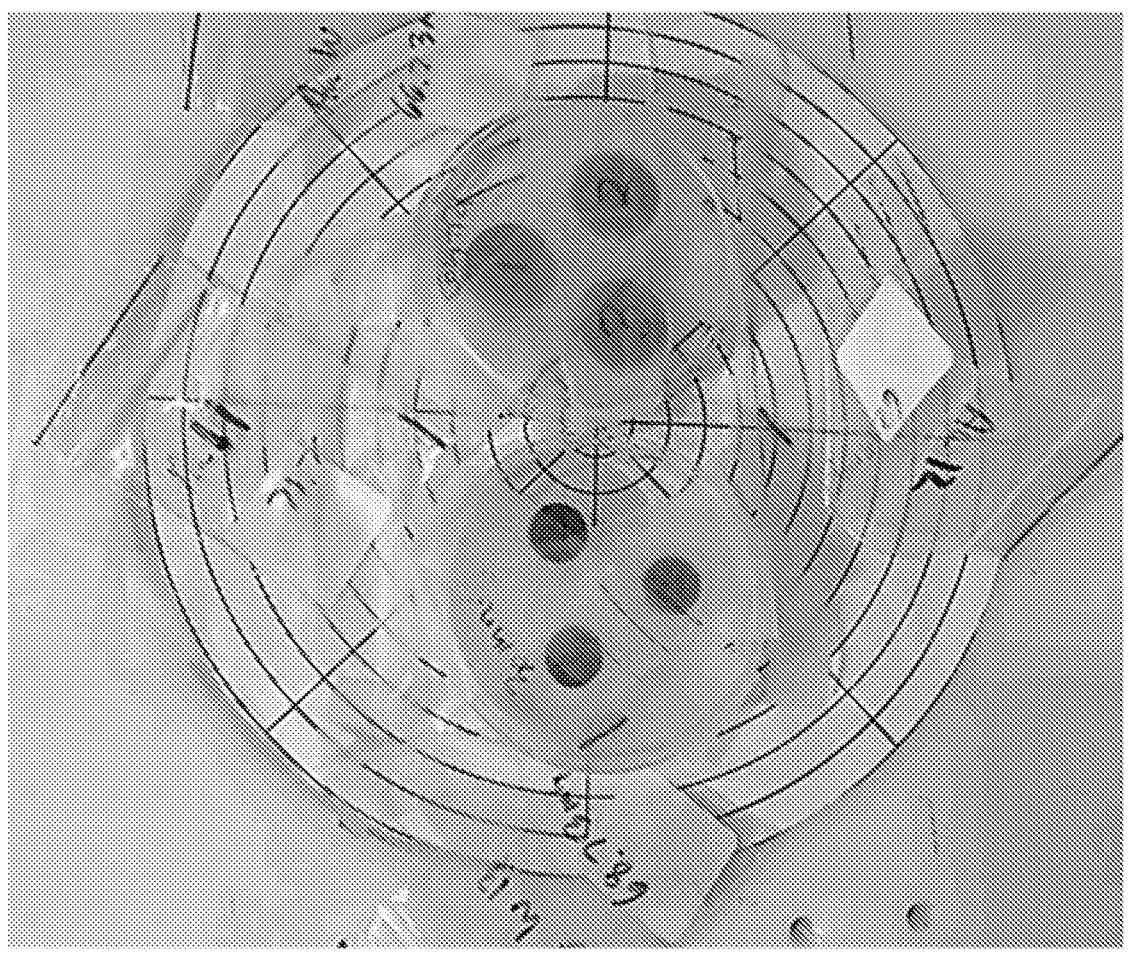
FIG. 3 is a photograph of a typical irradiation procedure of the Examples.

The inoculated disks were treated in the thermal neutron beam at MURR by mounting each petri dish into an irradiation position, as demonstrated in FIG. 3. The larger disks are Ti disks, while the smaller are $TiB_2$. Au/Cu flux wires are placed in the irradiation field to confirm neutron fluence. One group of $TiB_2$ disks were not exposed to radiation and was used as a control group a second group of Ti metal disks without B were irradiated for 60 minutes to serve as a neutron beam exposure only control. Two separate experiments were performed. In the first experiment, treatment groups were irradiated to 15 min, 30 min, 45 min, and 60 min of neutron exposure. A second experiment was conducted 6 months later with irradiation times of 15 min, 30 min, 37 min, 45 min, 53 min, and 60 min. The thermal The MCNPX calculations predict that a 60 min irradiation with a thermal neutron flux of $8.4 \times 10^8$ n/cm²/s on a $TiB_2$ target produces a physical dose of 12 kGy. This dose is confined to the volume of glycerin with a height of 6 μm above the $TiB_2$ surface. The higher $^{10}B$ atom density in 90% enriched $Ti^{10}B_2$ increases the total dose rate by a factor of 5.5. A 10 μm thick coating of 90% enriched $Ti^{10}B_2$ on Ti metal also significantly increases the dose rate compared to bulk $TiB_2$ with natural B.

Microbiology Study Results. Experiments were conducted with *Staphylococcus aureus* to assess the antimicrobial activity of $TiB_2$ with irradiation. The bacteria are suspended in glycerin and applied to the surface of sample and control disks. One control group consisted of $TiB_2$ disks that were not irradiated and a second control group consisted of Ti metal disks that were irradiated for 60 minutes. The number of colony forming units (CFUs) inoculated on the $TiB_2$ control disks decreased by 32-42% over the course of the experiment. However, there was not a significant difference in CFUs between the non-irradiated $TiB_2$ control disks and the irradiated Ti only disks in experiment 1 or experiment 2 (One Way ANOVA, $p<0.05$). Comparison of the irradiated Ti metal control group with the no irradiation $TiB_2$ control group demonstrates that there is no significant difference in survival for neutron beam exposure without the presence of B. In experiment 1, the surviving fraction (compared to the $TiB_2$ control group) after 15, 30, 45, and 60 minutes of neutron irradiation was 0.57, 0.33, 0.21, and $2.3 \times 10^{-3}$, respectively. In experiment 2, the surviving fraction (compared to the $TiB_2$ control group) after 15, 30, 37.5, 45, 52.5, and 60 minutes of neutron irradiation was 0.62, 0.46, 0.34, 0.18, 0.02, and $3.1\times10^5$, respectively. The data for both experiments have been plotted in a bacterial survival curve in FIG. 5. The data is also plotted in a survival curve in which the x-axis is converted from time into delivered physical dose via MNCP simulation FIG. 6 for experiment 1 and FIG. 7 for experiment 2. The shape of the bacterial survival curve with the data from the combined experiments has been fit using a linear model and a three-component polynomial. Surprisingly, there is little difference in fit between the linear and linear-quadratic models. A summary of the regression analysis is presented in Table 2.

TABLE 2

Regression parameters of the bacterial survival fit using a linear and linear-quadratic model.

| | $y_o$ | A | B | P | $R^2$ |
|---|---|---|---|---|---|
| Linear model $f = y_o + a \cdot x$ | 0.91 ± 0.04 | −0.016 ± 0.001 | NA | <0.0001 | 0.9631 |
| Quadratic model $f = y_o + a \cdot x + b \cdot x^2$ | 0.96 ± 0.04 | −0.023 ± 0.003 | $1 \times 10^{-4} \pm 4.5 \times 10^{-5}$ | <0.0001 | 0.9783 |

Discussion

Figure 5:
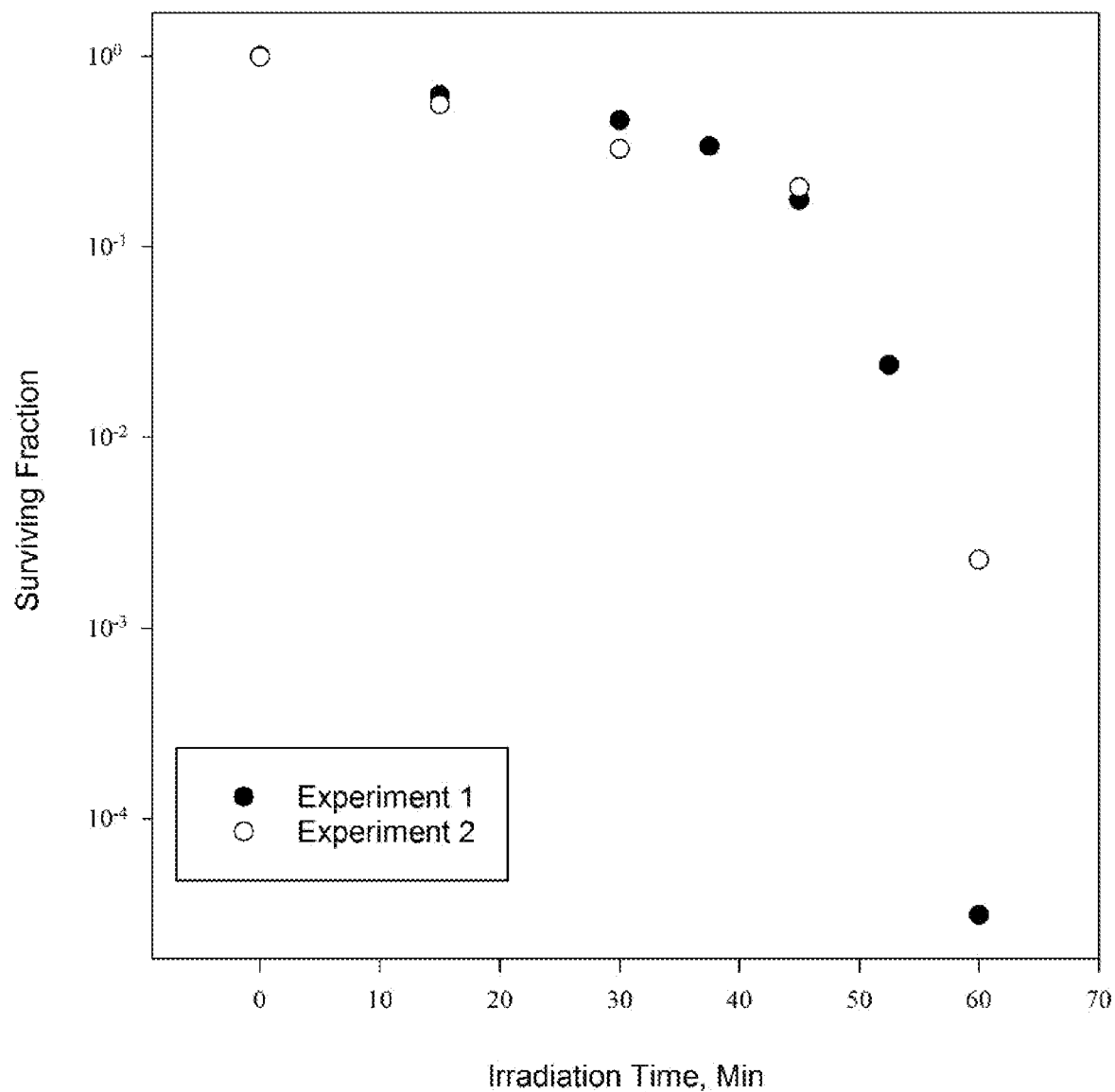
FIG. 5 is a graph of the bacterial CFU counts after BNCT irradiation for up to 60 minutes. The data were collected from two experiments of Example 1, conducted 6 months apart.
Figure 6:
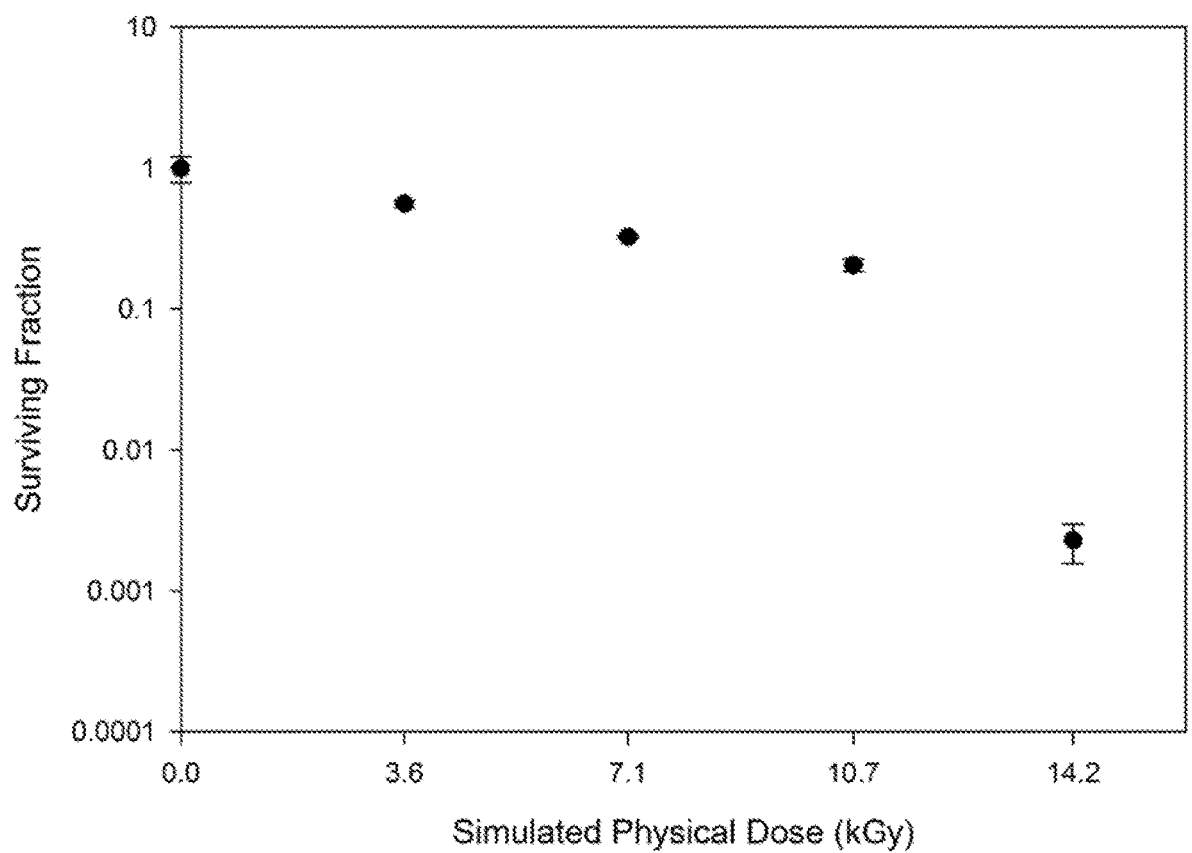
FIG. 6 is a graph of the bacterial CFU counts after BNCT irradiation for up to 60 minutes for the first experiment of Example 1, expressed as simulated delivered physical dose.
Figure 7:
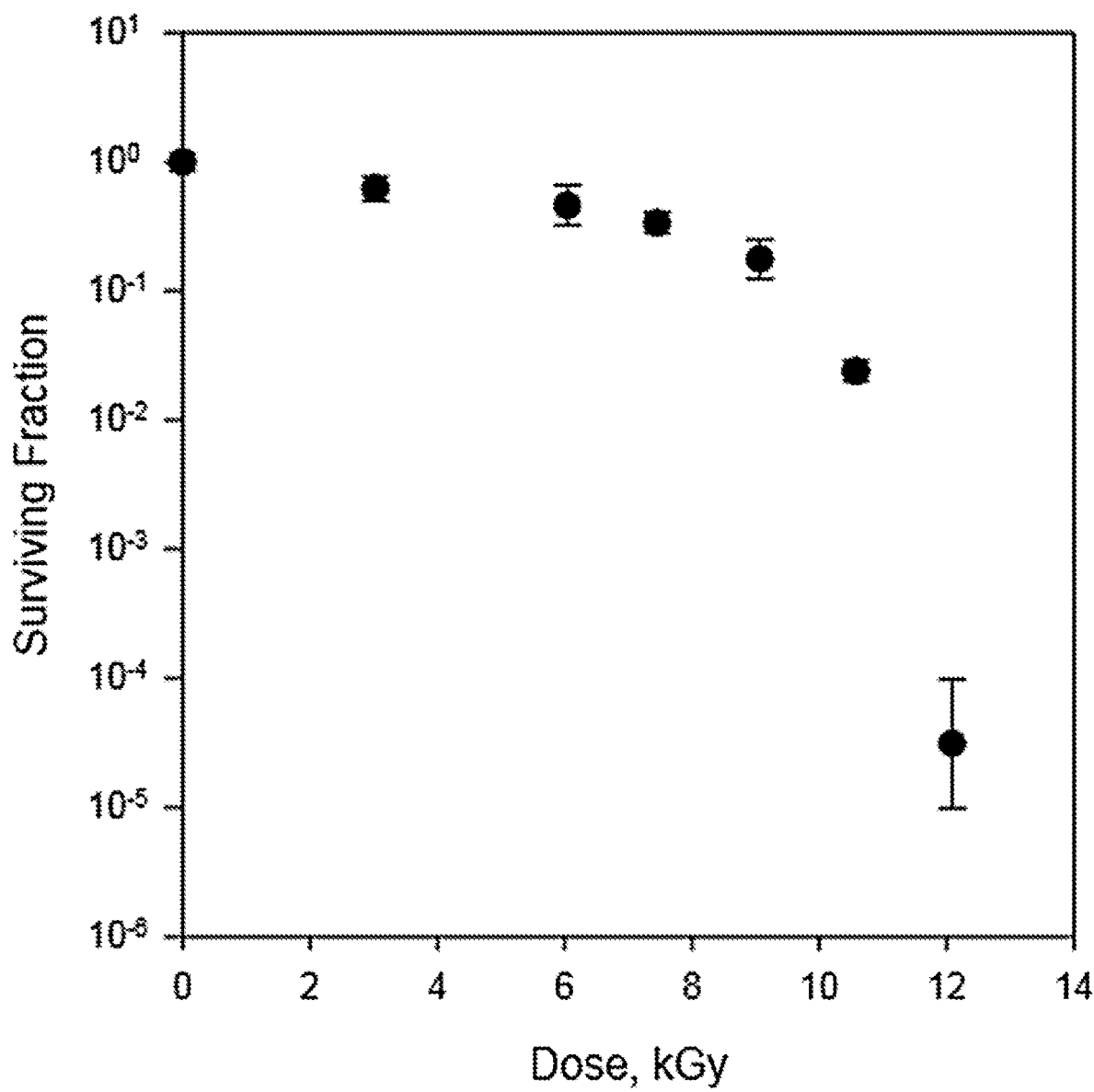
FIG. 7 is a graph of the bacterial CFU counts after BNCT irradiation for up to 60 minutes for the second experiment of Example 1, expressed as simulated delivered physical dose.

The bacterial survival data in FIGS. 5-7 do not match the expected bacterial survival curve for high LET radiation. A straight-line fit of the survival fraction on a log-linear scale is expected based on well-established high LET radiation bacterial cell survival curves. The second experiment, with increased data points, confirmed the unexpected shape of the survival curve. As reported in Table 1, the high LET particles from the $^{10}B$ capture reaction travel about 6 μm into the glycerin layer containing the *S. aureus*. At the time of inoculation, the bacteria and glycerin suspension has a calculated thickness of approximately 318 μm. Based on this thickness, most of the bacteria distributed through the glycerin layer do not directly interact with the high LET BNCT products. It is surprising that the cell lethality in this thick layer of glycerin is high despite the fact that a large portion of the bacteria are outside the range of the BCNT products. These unexpectedly efficacious results are similar to those reported when treating bacterial and fungal infections with radioimmunotherapy. We speculate that, in this case, the unusual survival curve could be caused by the production of free radicals or secondary electrons in the glycerin acting as the primary mechanism of cell death. Another possible explanation is that the high dose rate in this experiment, as calculated by MCNPX, may overcome some of the DNA repair mechanisms in *S. aureus*, which are significantly more efficient and accurate than in mammalian cell. Finally, the contribution of bystander effects to the observed cell lethality cannot be ruled out. In the future, molecular biology studies evaluating the mechanisms of cell death and direct analysis of DNA damage will be used to probe the mechanisms responsible for the unusual shape of the bacterial survival curve.

Medical implants are treated with 25 kGy of ionizing radiation for sterilization. The majority of these radiations are performed using gamma rays at room temperature in a dry environment. This work suggests that medical implants could be sterilized for infection in-vivo using thermal neutrons to activate $^{10}B$ at the surface of an implant. A 60 minute irradiation resulted in *S. aureus* survival of less than 0.3% in experiment 1 and 0.004% in experiment 2. The MCNPX calculation, Table 1, estimates that the physical dose in the first 6 μm above the $TiB_2$ surface is 12.1 kGy. However, we observed effective cell killing in a much thicker (~320 μm) layer of glycerin at the highest time points. Medical implants are not constructed from $TiB_2$. However, there are reports of modifying Ti metal by growing a surface layer of titanium boride to increase surface hardness and wear resistance in medical implants.[15] Since the expected range of the alpha particle in $TiB_2$ is 1.7 μm, the layer only needs to be a few microns thick for BNCIC to be effective. In Table 1, a theoretical 10 μm thick coating of 90% enriched $Ti^{10}B_2$ on the surface of Ti metal is sufficient to produce a 12.1 kGy dose in the first 6 μm of glycerin in about 13 minutes of irradiation time at a thermal neutron flux of $8.4\times10^8$ n/cm²/s. In the neutron beam at MURR, A 60 minute irradiation of tissue results in a non-specific gamma dose of 1.6 Gy and a background neutron dose of 1.5 Gy.[16] This background dose is comparable to a single fraction delivered for treatment of cancer. The use of 90% enriched $^{10}B$ cuts the irradiation time need to achieve the same dose as natural B by a factor of 5, see Table 1. This would also reduce the non-specific gamma dose and the background neutron dose by a factor of 5.

Future in vitro studies evaluating the levels of single-stranded DNA damage and double-stranded DNA damage could further elucidate the mechanism of damage caused by BNCIC on bacterial colonies. In vivo animal studies evaluating the treatment of surgically implanted disks, followed by a model of orthopedic implant infection are currently in planning, and could further demonstrate the ability of BNCIC to treat biofilm-embedded infections.

Example 2. Dose Modeling Study

In silico dose modeling of the experiment was performed prior to in vitro studies. The physical radiation dose was calculated using the Monte Carlo N-Particle (MCNPX 2.7) radiation transport code. The MCNPX model used the neutron spectrum measured at the thermal neutron beam facility at the MURR center. The model was normalized by benchmarking against experimentally measured activation foil monitors. The model geometry consisted of a $TiB_2$ disk positioned in the neutron beam. The $TiB_2$ target was covered with a 30 μm thick volume of glycerin that was divided into 1 μm thicknesses, about the size of a *S. aureus* cell. The physical dose is reported per 1 μm layer of glycerin extending from the $TiB_2$ surface. The physical dose (Gy) was calculated using the neutron capture ion algorithm (NCIA) option. The 7$^{th}$ entry on the phys:n card was set to 5 to transport the alpha particles and $^7Li$ nuclei while preserving angular momentum. The NCIA allows MCNPX to calculate the energy deposited by the alpha particle and the $^7Li$ ion created by the $^{10}B(n,\alpha)^7Li$ reaction. The physical radiation dose was calculated as the sum of the kinetic energy deposited by the a particle and the $^7Li$ ion in each 1 μm increment of glycerin above the $TiB_2$ surface.

Figure 4:
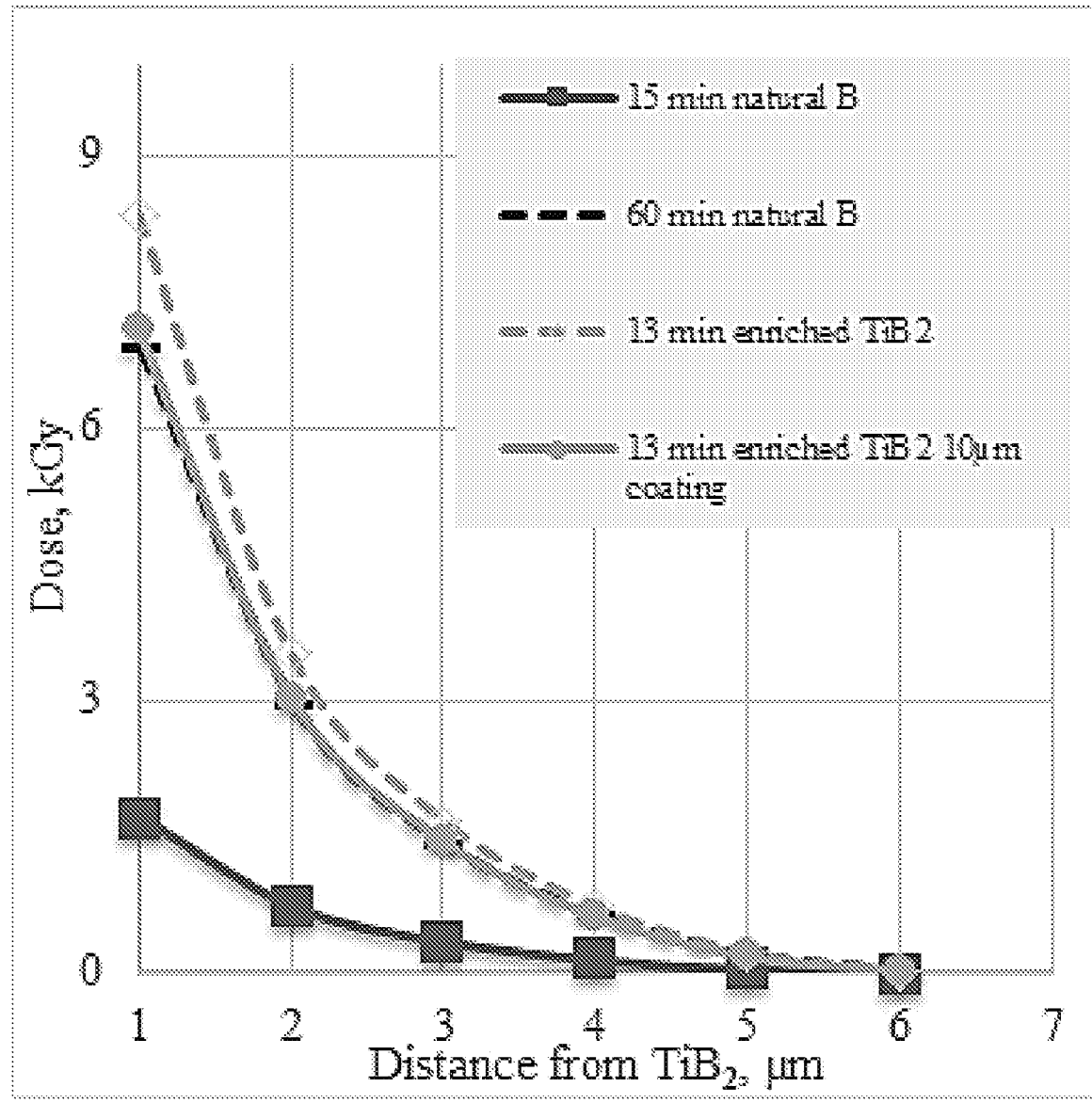
FIG. 4 is a graph of the radiation dose as a function of distance from boron source for the dose modeling study of Example 1.

The MNCPX model results are similar to those depicted in FIG. 4. The MCNPX model suggests that a dose of 14.2 kGy of radiation may be selectively delivered to the top 6.0 µm of the $TiB_2$ surface in 60 minutes using the MURR thermal neutron beam facility. A dose of 25 kGy from ionizing radiation is typically used to sterilize Medical implants, however the majority of these radiations are performed using gamma rays at room temperature in a dry environment; the sterilizing effect of high LET particles at body temperature in a hydrated system could be significantly more potent. A 60-minute irradiation of tissue using the BNCT facility at MURR results in a non-specific gamma dose of 1.6 Gy and a background neutron dose of 1.5 Gy. This background dose is comparable to a single fraction delivered for treatment of cancer. Isotopically enriched $^{10}B$ reduces the calculated time required to deliver 14.2 kGy of radiation from 60 minute to 13 minutes, shown in FIG. 8. This decrease in irradiation time also decreases the gamma ray and background neutron radiation dose by a factor of 4.6.

Example 3. Irradiation of Staph Bacterium Colonies on Titanium Diboride by Exposing to a Thermal Neutron Flux Four test samples were prepared: Samples #1 and #2 are staph colonies on titanium plates (representing unboronated implant surface); Samples #3 and #4 are staph colonies on titanium diboride plates (representing boronated implant surface). Samples #2 and #4 were exposed to thermal neutron flux at $10^8$ n/sec $cm^{-3}$ for approximate 1 hour to 180 minute, which delivered approximately 17 kGy in the 10 microns at the surface of the implant and resulted in extremely low exposure to any bulk tissue.

Following irradiation, each sample was swabbed and rehydrated in 1 ml of sterile buffer. The tube was vortexed and the 1 ml suspension was then serially diluted into tubes of 9 ml sterile buffered water. 100 µl of each dilution was then plated onto TSA plates and incubated for three days. The colonies on each plate were counted, with every plate containing >300 CFU (colony forming units) considered "Too Numerous to Count (TNTC)". The two dilutions from each sample that gave greater than 6 CFU/plate but less than 300 CFU/plate were averaged and calculated from the estimated CFU/dis.

Results are shown in Table 3. Samples #1 and #2 consisted of two titanium disks containing no Boron, while samples #3 and #4 were titanium diboride. Disks #2 and #4 were irradiated with a thermal neutron flux. The irradiated sample #4, which is with the titanium diboride surface, has the highest staph colony reduction.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

REFERENCES

Rabih O. Darouiche New England Journal of Medicine 350 (14), 1422 (2004).
Cédric Jacqueline and Jocelyne Caillon, Journal of Antimicrobial Chemotherapy 69 (suppl 1), i37 (2014).
T. N. Peel, M. M. Dowsey, K. L. Buising, D. Liew, and P. F. Choong, Clinical microbiology and infection: the official publication of the European Society of Clinical Microbiology and Infectious Diseases 19 (2), 181 (2013).
E. Zimlichman, D. Henderson, O. Tamir, and et al., JAMA Internal Medicine 173 (22), 2039 (2013).
Rolf Barth, M. Vicente, Otto Harling, W. Kiger, Kent Riley, Peter Binns, Franz Wagner, Minoru Suzuki, Teruhito Aihara, Itsuro Kato, and Shinji Kawabata, Radiation oncology (London, England) 7, 146 (2012).
J. Coderre and G. Morris, Radiation Research 151 (1), 1 (1999).
Leena Kankaanranta, Tiina Seppälä, Hanna Koivunoro, Kauko Saarilahti, Timo Atula, Juhani Collan, Eero Salli, Mika Kortesniemi, Jouni Uusi-Simola, Petteri Valimaki, Antti Makitie, Marko Seppänen, Heikki Minn, Hannu Revitzer, Mauri Kouri, Petri Kotiluoto, Tom Seren, Iiro Auterinen, Sauli Savolainen, and Heikki Joensuu, International journal of radiation oncology, biology, physics 82 (1), 75 (2012); Leena Kankaanranta, Tiina Seppälä, Hanna Koivunoro, Petteri Välimäki, Annette Beule, Juhani Collan, Mika Kortesniemi, Jouni Uusi-Simola, Petri Kotiluoto, Iiro Auterinen, Tom Serèn, Anders Paetau, Kauko Saarilahti, Sauli Savolainen, and Heikki

TABLE 3

| | Staph Colony Counts | | | | | | | |
| --- | --- | --- | --- | --- | --- | --- | --- | --- |
| | | | | dilution | | | | |
| Sample | 10^-3 | 10^-04 | 10^-05 | 10^-06 | 10^-07 | 10^-08 | 10^-09 | CFU/disc |
| Sample #1 | TNTC | TNTC | TNTC | TNTC | 187 | 20 | 2 | 1.94E+09 |
| Sample #2 | TNTC | TNTC | TNTC | TNTC | 258 | 25 | 1 | 2.54E+09* |
| Sample #3 | TNTC | TNTC | TNTC | TNTC | TNTC | 96 | 9 | 9.30E+09 |
| Sample #4 | TNTC | 258 | 36 | 1 | 1 | 0 | 0 | 3.09E+06** |

Joensuu, International journal of radiation oncology, biology, physics 80 (2), 369 (2011).

S. Halfon, M. Paul, D. Steinberg, A. Nagler, A. Arenshtam, D. Kijel, I. Polacheck, and M. Srebnik, Applied Radiation and Isotopes 67 (7), S278 (2009).

Peter Kueffer, Charles Maitz, Aslam Khan, Seth Schuster, Natalia Shlyakhtina, Satish Jalisatgi, John Brockman, David Nigg, and M. Hawthorne, Proceedings of the National Academy of Sciences of the United States of America (2013).

J. Brockman, D. Nigg, M. Hawthorne, and C. McKibben, Applied radiation and isotopes: including data, instrumentation and methods for use in agriculture, industry and medicine 67 (7-8 Suppl), 5 (2009).

J. D. Brockman, D. W. Nigg, and M. F. Hawthorne, in *International Conference on Mathematics and Computational Methods Applied to Nuclear Science & Engineering* (Sun Valley, Idaho, USA, 2013).

J. D. Brockman, D. W. Nigg, M. F. Hawthorne, M. W. Lee, and C. McKibben, Journal of Radioanalytical and Nuclear Chemistry 282 (1), 157 (2009).

M C Joiner and A J van der Kogel, *Basic Clinical Radiobiology*, 4th ed. (CRC Press, Boca Raton, FL, 2009).

E. Dadachova and A. Casadevall, Seminars in nuclear medicine 39 (2), 146 (2009).

C. Lee, N. Tikekar, K. S. R. Chandran, and A. Sanders, presented at the Medical Device Materials IV: Proceedings of the Materials and Processes for Medical Devices Conference 2007, 2008 (unpublished); A. P. Sanders, N. Tikekar, C. Lee, and K. S. R. Chandran, Journal of Manufacturing Science and Engineering, Transactions of the ASME 131 (3), 0310011 (2009).

J D Brockman, D W Nigg, M F Hawthorne, M W Lee, and C McKibben, Journal of radioanalytical and nuclear chemistry 282 (1), 157 (2009).

D. B. Pelowitz, MCNPX User's Manual Version 2.5.0 (2005).

B. M. Van Der Ende, J. Atanackovic, A. Erlandson, and G. Bentoumi, Nuclear Instruments and Methods in Physics Research, Section A: Accelerators, Spectrometers, Detectors and Associated Equipment 820, 40 (2016);

Haisheng Zheng, Balavinayagam Ramalingam, Somik Mukherjee, Yang Zhou, Keshab Gangopadhyay, John D Brockman, Mark W Lee, and Shubhra Gangopadhyay, Sensing and Bio-Sensing Research 9, 1 (2016).

We claim:

1. A method for treating infection at an implantation site comprising: implanting a device comprising an isotope capable of producing a dose of ionizing radiation upon exposure to a flux of low energy neutrons into an human or animal subject, wherein the device is not a stent; and exposing said device to a flux of low energy neutrons to produce a dose of ionizing radiation suitable for treating bacterial infection at said implantation site; wherein the device comprises a body made of a material having a low neutron absorption cross-section and a surface layer of 1 µm to 100 µm thickness on the body, the isotope is selected from the group consisting of B-10, Li-6, Gd-157 and Dy-164 being disposed in the surface layer, such that the isotope is present at the surface of the device upon implantation.

2. The method of claim 1, wherein said dose of ionizing radiation within 6 µm of a surface of said device is greater than 2 kGy.

3. The method of claim 1, wherein the thermal neutron fluence delivered in said exposing step is greater than $7.5 \times 10^{11}$ n/cm$^2$.

4. The method of claim 1, wherein said device is exposed to said flux of low energy neutrons for five minutes to 30 minutes.

5. The method of claim 1, wherein the flux of low energy neutrons is 0.001 eV to 100 keV, 0.001 eV to 0.5 eV, 0.5 eV to 100 keV, 0.5 eV to 100 eV, or 100 eV to 100 keV.

6. The method of claim 1, wherein said flux of low energy neutrons produced at the implantation site during said exposing step is $1 \times 10^8$ to $15 \times 10^8$ neutrons cm$^{-2}$ s$^{-1}$.

7. The method of claim 1, wherein a survival fraction of bacteria at said implantation site after said exposing step is $0.62 \times 10^5$ to $3.1 \times 10^5$ compared to a non-irradiated control.

8. The method of claim 1, wherein 0.3% or fewer of the bacterial infection at said implantation site survive said exposing step.

9. The method of claim 1, wherein said dose of ionizing radiation within 6 µm of a surface of said device is greater than 10 kGy, and said exposure is less than 30 minutes.

10. The method of claim 1, wherein said dose of ionizing radiation within 6 µm of a surface of said device is greater than 10 kGy, and a background dose delivered within said 6 µm is less than 100 cGy.

11. The method of claim 1, wherein said exposing step is performed in response to an indication of infection at said implantation site.

12. The method of claim 1, wherein said exposing step is repeated in response to a subsequent indication of infection at said implantation site.

13. The method of claim 1, wherein said device is implanted at a depth of less than 2 cm and said flux of low energy neutrons is 0.0001 eV to 0.5 eV.

14. The method of claim 1, wherein said device is implanted at a depth of greater than 1 cm and said flux of low energy neutrons is 0.5 eV to 10 keV.

15. The method of claim 1, wherein said device is an orthopedic implant.

16. The method of claim 1, wherein the body is made primarily of titanium.

17. The method of claim 1, wherein the isotope is anti-infective only after being exposed to the flux of low energy neutrons.

18. The method of claim 1, wherein the material comprises 30% or greater of the isotope, 50% or greater of the isotope, or 90% or greater of the isotope.

* * * * *